(12) United States Patent
Pazenok et al.

(10) Patent No.: US 8,399,679 B2
(45) Date of Patent: Mar. 19, 2013

(54) ARYL-SUBSTITUTED PYRAZOLES

(75) Inventors: Sergii Pazenok, Solingen (DE); Norbert Lui, Odenthal (DE)

(73) Assignee: Bayer CropScience AG (DE)

( * ) Notice: Subject to any disclaimer, the term of this patent is extended or adjusted under 35 U.S.C. 154(b) by 0 days.

(21) Appl. No.: 13/618,053

(22) Filed: Sep. 14, 2012

(65) Prior Publication Data
US 2013/0018192 A1    Jan. 17, 2013

Related U.S. Application Data

(62) Division of application No. 12/842,243, filed on Jul. 23, 2010, now Pat. No. 8,299,260.

(30) Foreign Application Priority Data

Jul. 23, 2009 (EP) ..................................... 09166238

(51) Int. Cl.
*C07D 401/04* (2006.01)
*C07D 231/14* (2006.01)

(52) U.S. Cl. .................................. 546/275.4; 548/374.1

(58) Field of Classification Search ............... 546/275.4; 548/374.1
See application file for complete search history.

(56) References Cited

U.S. PATENT DOCUMENTS

| 5,580,843 | A | 12/1996 | Stetter et al. |
| 7,038,057 | B2 | 5/2006 | Annis et al. |
| 8,299,260 | B2 | 10/2012 | Pazenok et al. |
| 2009/0275471 | A1 | 11/2009 | Funke et al. |
| 2010/0029478 | A1 | 2/2010 | Alig et al. |

FOREIGN PATENT DOCUMENTS

| EP | 0 659 745 A1 | 12/1994 |
| WO | WO 99/62885 A1 | 12/1999 |

OTHER PUBLICATIONS

Adamo, M.F.A., et al., "Practical routes to diacetylenic ketones and their application for the preparation of alkynyl substituted pyridines, pyrimidines and pyrazoles," *Tetrahedron* 59:2197-2205, Elsevier Science Ltd., USA (2003).

Bishop, B.C., et al., "Regioselective Synthesis of 1,3,5-Substituted Pyrazoles from Acetylenic Ketones and Hydrazines," *Synthesis* 2004(1):43-52, Georg Thieme Verlag Stuttgart New York, USA (2004).

Flores, A.F.C., et al., "Haloacetylated Enol Ethers, 19:[1] Synthesis of 3-(2-Thienyl)- and 3-(2-Furyl)-5-trihalomethyl Substituted Azoles," *Synthesis* 2005(16):2744-2750, Georg Thieme Verlag Stuttgart New York, USA (2005).

Liang, J.T., et al., "Design of Concise, Scalable Route to a Cholecystokinin 1 (CCK 1) Receptor Antagonist," *J. Org. Chem.* 72:8243-8250, American Chemical Society, USA (2007).

Martins, M.A.P., et al., "A Convenient Synthesis of 5-Trichloromethyl-5-hydroxy-3-heteroalkyl-4,5-dihydroisoxazoles," *Synthesis* 2001(13):1959-1964, Georg Thieme Verlag Stuttgart New York, USA (2001).

Martins, M.A.P., et al., "Synthesis of new halo-containing acetylenes and their application to the synthesis of azoles," *Tetrahedron Letters* 45:4935-4938, Elsevier Ltd., USA (2004).

International Search Report for International Application No. PCT/EP2010/004285, European Patent Office, the Netherlands, mailed on Aug. 17, 2010.

Bonacorso, H.G., et al., "Trifluoroacetylation of Unsymmetrical Ketone Acetals. A Convenient Route to Obtain Alkyl Side Chain Trifluoromethylated Heterocycles," *J. Fluorine Chem.* 99(2):177-182, Elsevier Sequoia S.A., United States (1999).

*Primary Examiner* — Janet Andres
*Assistant Examiner* — Timothy R Rozof
(74) *Attorney, Agent, or Firm* — Sterne, Kessler, Goldstein & Fox P.L.L.C.

(57) ABSTRACT

The present invention relates to a process for preparing 1-aryl-substituted pyrazoles, comprising the reaction of alkoxy enones and enamino ketones with arylhydrazine derivatives to give 1-aryl-substituted dihydro-1H-pyrazoles, the further reaction thereof with elimination of water to give 1-aryl-substituted trihalomethylpyrazoles, and the further processing thereof.

4 Claims, No Drawings

ARYL-SUBSTITUTED PYRAZOLES

The present invention relates to a process for preparing 1-(aryl)-substituted pyrazoles, comprising the reaction of alkoxy enones and enamino ketones with hydrazine derivatives to give 1-(aryl)-substituted dihydro-1H-pyrazoles, the further reaction thereof with elimination of water to give 1-(aryl)-substituted trihalomethylpyrazoles, and the further processing thereof.

1-(Aryl)-substituted pyrazoles and 1H-pyrazoles are valuable intermediates for preparation of anthranilamides, which can find use as insecticides.

The literature has already described the formation of pyrazoles by reaction of 1,3-dicarbonyls or corresponding 1,3-bis-electrophilic reagents with monoalkyl- or monoarylhydrazines (Synthesis 2004, N1. pp 43-52). However, it is reported that, in the case of monoalkyl- or monoarylhydrazines, the result is a mixture of regioisomeric pyrazoles (Tetrahedron 59 (2003), 2197-2205; Martins et al., T. L. 45 (2004) 4935). Attempts to obtain exclusively one regioisomer failed (JOC 2007, 72822 8243-8250). Likewise described in the literature is a process for preparing trifluoromethylpyrazoles (WO 2003/016282). Likewise described are preparation processes for (het)aryl-substituted pyrazoles (WO 2007/144100), wherein the corresponding pyrazoles are obtained by reducing diesters with DIBAL or LiAlH$_4$. However, very low temperatures are required, and the use of DIBAL is uneconomic.

It is therefore an object of the present invention to provide novel, economically viable processes for preparing 1-(aryl)-substituted pyrazole derivatives and 1-(aryl)-substituted dihydro-1H-pyrazoles, which do not have the disadvantages described above, and which are notable for a process regime which can be performed in a particularly efficient and simple manner even on the industrial scale.

The object was achieved in accordance with the invention by a process for preparing 1-aryl-substituted pyrazole derivatives of the general formula (I)

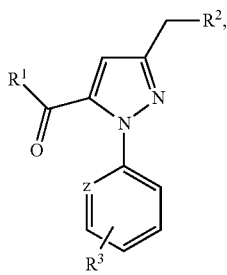

in which
$R^1$ is hydroxyl, alkoxy, aryloxy, halogen,
$R^1$ is preferably hydroxyl, (C$_1$-C$_6$)alkoxy, halogen,
$R^1$ is more preferably hydroxyl, (C$_1$-C$_6$)alkoxy,
$R^2$ is hydroxyl, alkoxy, arylalkoxy, alkylthio, halogen, O—(C=O)alkyl, O—(C=O)O-alkyl, (C=O)haloalkyl, OSO$_2$ alkyl, OSO$_2$—haloalkyl, OSO$_2$-aryl,
$R^2$ is preferably hydroxyl, halogen, O—(C=O)(C$_1$-C$_6$)alkyl,
$R^2$ is more preferably hydroxyl, O(C=O)CH$_3$,
$R^3$ is H, halogen, CN, NO$_2$, alkyl, cycloalkyl, haloalkyl, halocycloalkyl, alkoxy, haloalkoxy, alkylamino, dialkylamino, cycloalkylamino,
$R^3$ is preferably H, halogen, CN, NO$_2$, (C$_1$-C$_6$)-alkyl, halo (C$_1$-C$_6$)-alkyl, (C$_1$-C$_6$)alkoxy, halo(C$_1$-C$_6$)alkoxy,
$R^3$ is more preferably F, chlorine, bromine, iodine, CN, (C$_1$-C$_4$)-alkyl, halo(C$_1$-C$_4$)-alkyl, halo(C$_1$-C$_4$)alkoxy,
$R^3$ is most preferably fluorine, chlorine, bromine, iodine,
$R^3$ is especially preferably chlorine,
Z is CH, N,
Z is preferably and more preferably N,
characterized in that
alkoxy enones and enamino ketones of the formula (II)

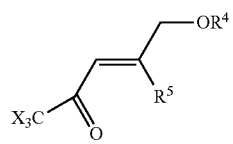

in which
$R^4$ is H, alkyl, arylalkyl, —(C=O)alkyl, (C=O)haloalkyl, —(C=O)O-alkyl, SO$_2$ alkyl, SO$_2$-haloalkyl, SO$_2$-aryl,
X is fluorine, chlorine, bromine, iodine,
$R^5$ is alkoxy, dialkylamino, cycloalkylamino, thioalkyl, or is cycloalkyl which may optionally contain 1-3 heteroatoms from the group of O, N, S,
are reacted with arylhydrazines of the formula (III)

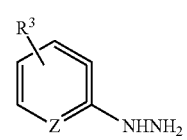

in which
$R^3$ is H, halogen, CN, NO$_2$, alkyl, cycloalkyl, haloalkyl, halocycloalkyl, alkoxy, haloalkoxy, alkylamino, dialkylamino, cycloalkylamino,
Z is CH, N,
to give 1-aryl-substituted dihydro-1H-pyrazoles of the formula (IV)

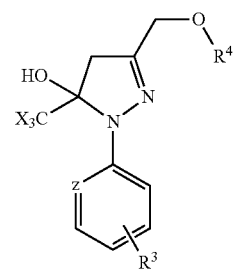

in which X, $R^3$, $R^4$, Z are each as defined above, the latter are optionally converted further, without preceding isolation, with elimination of water, to 1-aryl-substituted trihalomethylpyrazoles of the formula (V)

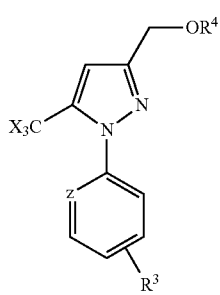

(V)

in which X, $R^3$, $R^4$, Z are each as defined above, these compounds of the general formula (V) are converted with addition of HCl, $H_2SO_4$ or a base, for example, to pyrazolecarboxylic acids of the formula (VI)

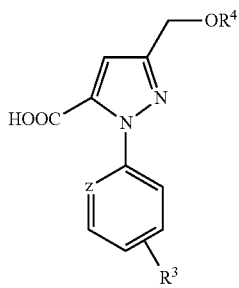

(VI)

in which $R^3$, $R^4$, Z are each as defined above, the latter are converted, after detaching the $R^4$ group, to hydroxymethylpyrazole acids of the formula (VII)

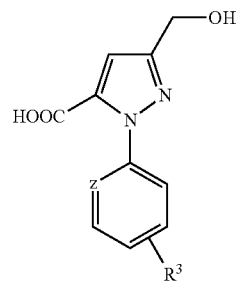

(VII)

in which $R^3$, Z are as defined above, and the latter are converted to compounds of the formula (I)

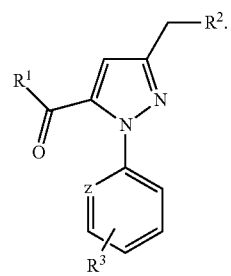

(I)

More particularly, the inventive reaction is notable for the use of inexpensive raw materials such as alkoxyalkylene, for example alkoxypropene, acid chlorides and aryl hydrazines, and for a process regime which can be performed in a particularly efficient and simple manner even on the industrial scale.

The process according to the invention can be illustrated by the following scheme (I):

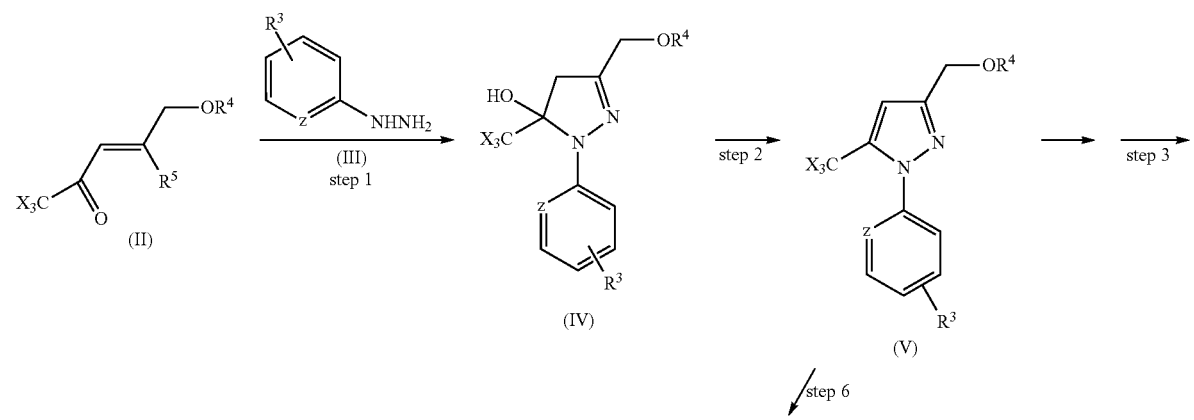

Scheme (I)

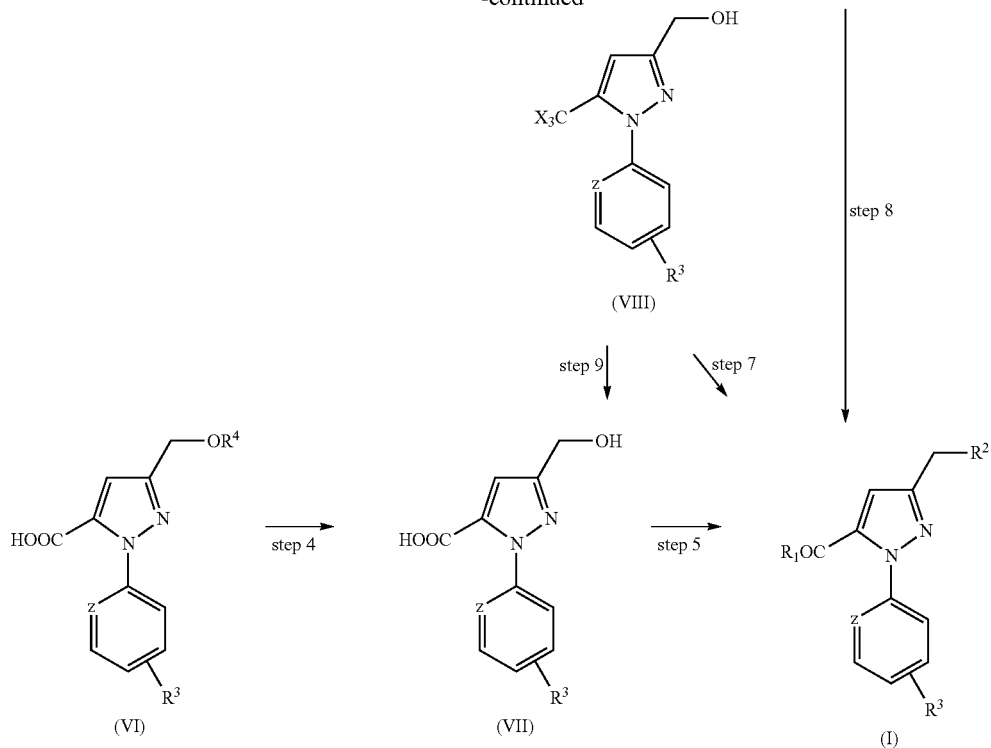
where X, $R^1$, $R^2$, $R^3$, $R^4$, $R^5$, Z are each as defined above.
The conversion of a compound of the formula (VII) to a compound of the formula (I) is effected by customary methods and is illustrated by way of example using the following scheme (I).
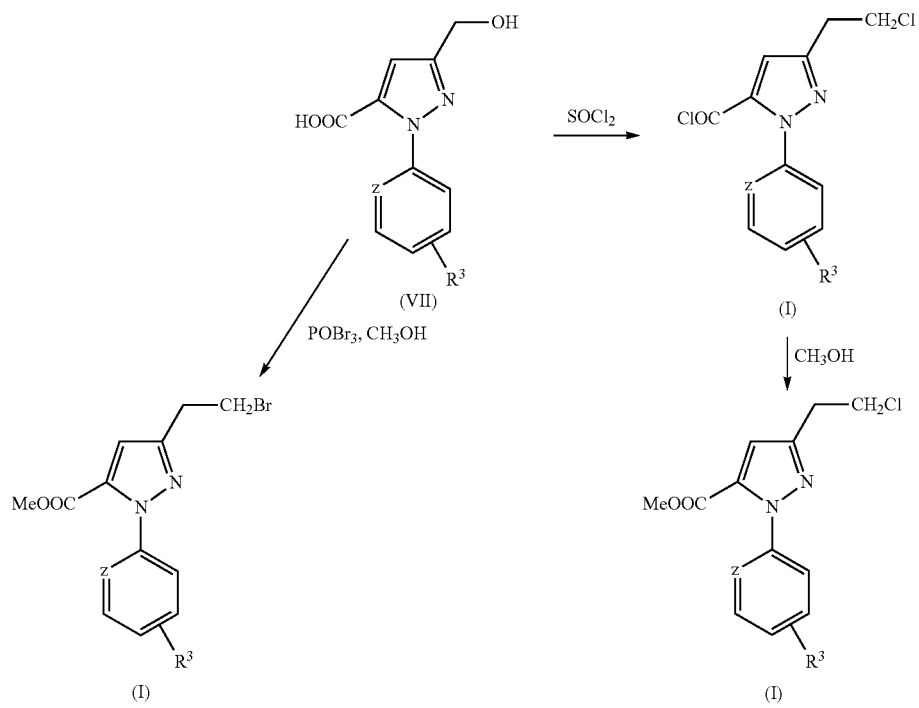
where $R^3$, Z are each as defined above.

General Definitions

In connection with the present invention, the term "halogens" (X), unless defined otherwise, comprises those elements which are selected from the group consisting of fluorine, chlorine, bromine and iodine, preference being given to using fluorine, chlorine and bromine, and particular preference to using fluorine and chlorine. Substituted groups may be mono- or polysubstituted, and the substituents may be the same or different in the case of polysubstitutions.

Alkyl groups substituted by one or more halogen atoms (—X) (=haloalkyl groups) are, for example, selected from trifluoromethyl ($CF_3$), difluoromethyl ($CHF_2$), $CCl_3$, $CFCl_2$, $CF_3CH_2$, $ClCH_2$, $CF_3CCl_2$.

In connection with the present invention, alkyl groups, unless defined differently, are linear or branched hydrocarbon groups.

The definitions of alkyl and $C_1$-$C_{12}$-alkyl encompass, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined differently, cycloalkyl groups are cyclic saturated hydrocarbon groups which may optionally contain 1-3 heteroatoms from the group of O, N, S.

In connection with the present invention, unless defined differently, aryl radicals are $C_6$-$C_{10}$ aromatic hydrocarbon radicals, and aromatic hydrocarbon radicals which may have one, two or more heteroatoms which are selected from O, N, P and S and may optionally be substituted by further groups.

In connection with the present invention, unless defined differently, arylalkyl groups and arylalkoxy groups are alkyl or alkoxy groups which are substituted by aryl groups and may have an alkylene chain. Specifically, the definition of arylalkyl encompasses, for example, the meanings of benzyl and phenylethyl, and the definition of arylalkoxy, for example, the meaning of benzyloxy.

In connection with the present invention, unless defined differently, alkylaryl groups (alkaryl groups) and alkylaryloxy groups are aryl groups or aryloxy groups which are substituted by alkyl groups and may have a $C_{1-8}$-alkylene chain and may have, in the aryl skeleton or aryloxy skeleton, one or more heteroatoms which are selected from O, N, P and S.

The inventive compounds may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

Alkoxy Enones and Enamino Ketones of the Formula (II)

The enones used as starting materials in the performance of the process according to the invention are defined in general terms by the formula (II)

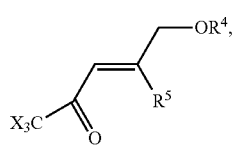

(II)

where X is fluorine, chlorine, bromine, iodine, preferably fluorine, chlorine or Br, more preferably chlorine, $R^4$ is H, alkyl, arylalkyl, (C=O)alkyl, (C=O)haloalkyl, —(C=O)O-alkyl, $SO_2$ alkyl, $SO_2$-haloalkyl, $SO_2$-aryl, $R^4$ is preferably aryl($C_1$-$C_6$)-alkyl, (C=O)($C_1$-$C_6$)-alkyl, (C=O)halo($C_1$-$C_6$)-alkyl, —(C=O)O—($C_1$-$C_6$)-alkyl, $SO_2$ ($C_1$-$C_6$)-alkyl, $SO_2$ phenyl, $SO_2$-halo($C_1$-$C_6$)-alkyl, $R^4$ is more preferably (C=O)($C_1$-$C_6$)-alkyl, (C=O)halo($C_1$-$C_6$)-alkyl, —(C=O)O—($C_1$-$C_6$)-alkyl, $SO_2$ ($C_1$-$C_6$)-alkyl, $R^4$ is most preferably (C=O)($C_1$-$C_6$)-alkyl, (C=O)halo($C_1$-$C_6$)-alkyl, $R^4$ is especially preferably (C=O)$CH_3$, $R^5$ is alkoxy, dialkylamino, cycloalkylamino, thioalkyl, or is cycloalkyl which may optionally contain 1-3 heteroatoms from the group of O, N, S, $R^5$ is preferably ($C_1$-$C_6$)-alkoxy, Di($C_1$-$C_6$)-alkylamino, morpholino, thioalkyl, $R^5$ is more preferably ($C_1$-$C_4$)-alkoxy, $R^5$ is most preferably methoxy.

Examples of alkoxy enones and enamino ketones of the formula (II) which are suitable in accordance with the invention are 5,5,5-trichloro-2-methoxy-4-oxopent-2-en-1-yl acetate,
1,1,1-trichloro-5-hydroxy-4-methoxypent-3-en-2-one,
5-(benzyloxy)-1,1,1-trichloro-4-methoxypent-3-en-2-one,
5,5,5-trifluoro-2-methoxy-4-oxopent-2-en-1-yl acetate,
(2Z)-5,5,5-trichloro-2-methoxy-4-oxopent-2-en-1-yl trichloroacetate.

The compounds of the formula (II) are novel, with the exception of that compound of the formula (II) in which X is Cl, $R^4$ is phenyl and $R^5$ is methoxy, which has already been described in the literature (cf. Synthesis 2001, 13, 1959).

The compounds of the formula (II) can be prepared, for example, by reacting 5-bromo-1,1,1-trihalo-4-alkoxypent-3-en-2-one with suitable O-nucleophiles under particular reaction conditions.

Arylhydrazines of the general formula (III)

The hydrazinopyridines used according to the present invention are compounds of the general formula (III)

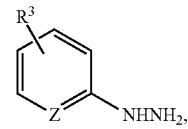

(III)

in which $R^3$ is H, halogen, CN, $NO_2$, alkyl, cycloalkyl, haloalkyl, halocycloalkyl, alkoxy, haloalkoxy, alkylamino, dialkylamino, cycloalkylamino, $R^3$ is preferably H, halogen, CN, $NO_2$, ($C_1$-$C_6$)-alkyl, halo($C_1$-$C_6$)-alkyl, ($C_1$-$C_6$)alkoxy, halo($C_1$-$C_6$)alkoxy, $R^3$ is more preferably F, chlorine, bromine, iodine, CN, ($C_1$-$C_4$)-alkyl, halo($C_1$-$C_4$)-alkyl, halo($C_1$-$C_4$)alkoxy, $R^3$ is most preferably fluorine, chlorine, bromine, iodine, $R^3$ is especially preferably chlorine, Z is CH, N, Z is preferably and more preferably N.

Examples of hydrazinopyridines suitable in accordance with the invention are 3-chloro-2-hydrazinopyridine, phenylhydrazine, o- and p-chlorophenylhydrazine, nitrophenylhydrazine, O-methylphenylhydrazine.

Step (1)

In a first embodiment of the present process, alkoxy enones and enamino ketones of the formula (II) are first reacted with arylhydrazines of the formula (III). Thereafter, the intermediates formed in step (1) are converted to the 5-trihalomethylpyrazole derivatives of the formula (V) with elimination of water (step 2).

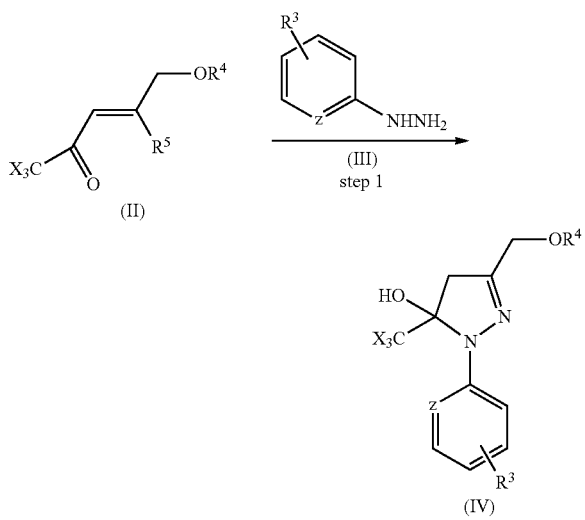

in which Z, X, $R^3$, $R^4$ and $R^5$ are each as defined above.

It has been found that, surprisingly, the reaction of alkoxy enones and enamino ketones of the formula (II) with arylhydrazines of the formula (III) proceeds regioselectively to give 1-(aryl)-dihydropyrazolols of the formula (IV). The second regioisomer was not observed. It is also known that organic acetates, sulphonates or carbonates react with N-nucleophiles (for example amines or hydrazines) with elimination of the acetate group, sulphonate group or of the carbonate group to give amides and hydrazides. Consequently, it is considered to be surprising that, in the case of the reaction of alkoxy enones of the formula (II) where $R^4$ is (C=O)alkyl, (C=O)haloalkyl, —(C=O)O-alkyl, $SO_2$ alkyl, $SO_2$-haloalkyl, $SO_2$-aryl with arylhydrazines of the formula (III) which have strong nucleophilicity, only cyclization takes place, and aryl-5-hydroxy-5-(haloalkyl)-4,5-dihydro-1H-pyrazol-3-yl derivatives of the formula (IV) which were unknown to date form in a high yield.

Process step (1) of the invention is performed preferably within a temperature range from −20° C. to +100° C., more preferably at temperatures of −10° C. to +80° C.

Process step (1) of the invention is generally performed under standard pressure. Alternatively, it is, however, also possible to work under reduced pressure in order to remove the water and alcohol.

The reaction time is not critical and may be selected, according to the batch size and temperature, within a range between a few minutes and several hours.

In the performance of the process step of the invention, 1 mol of the enone of the formula (II) is reacted with 0.8 mol to 1.5 mol, preferably 0.9 mol to 1.2 mol, more preferably with the equimolar amount, of the arylhydrazine of the formula (II).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide, or sulphones such as sulpholane, alcohols such as methanol, ethanol, isopropanol. Particular preference is given to using toluene, ethanol, methyl tert-butyl ether, THF, acetonitrile. The aryl-5-hydroxy-5-(haloalkyl)-4,5-dihydro-1H-pyrazol-3-yl]derivatives formed can be used without preceding work-up in the subsequent step (2), in which water is eliminated. In some cases, the elimination of water takes place actually during the cyclization.

Alternatively, these intermediates can be isolated by suitable workup steps and optionally further purification. It is then possible to eliminate water only at a later stage.

Step 2. Water Elimination

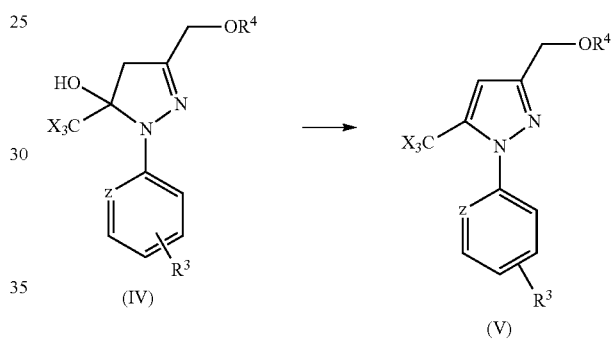

in which Z, X, $R^3$, $R^4$ are each as defined above.

For the water elimination, the following reagents are useful: $H_2SO_4$, $CF_3COOH$, PivCl, $POCl_3$, polyphosphoric acid, $SOCl_2$, $(CH_3CO)_2O$, $(CF_3CO)_2O$, oxalyl chloride, phosgene and diphosgene.

Preference is given to $(CF_3CO)_2O$, thionyl chloride, oxalyl chloride and phosgene.

Process step (A) of the invention is preferably performed within a temperature range from −20° C. to +100° C., more preferably at temperatures of −10° C. to +70° C.

Process step (2) of the invention is generally performed under standard pressure. Alternatively, it is, however, also possible to work under reduced pressure or under elevated pressure (e.g. reaction with phosgene). It is also possible to eliminate water merely thermally.

The reaction time is not critical and may, depending on the batch size and temperature, be selected within a range between a few minutes and several hours.

In the performance of the process step of the invention, 1 mol of the 3-[(alkoxy)methyl]-1-(aryl)-5-(trihaloalkyl)-4,5-dihydro-1H-pyrazol-5-ol of the formula (IV) is reacted with 0.9 to 2.5 mol, preferably 1 mol to 1.8 mol, more preferably with the equimolar amount, of the dewatering agent.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; ketones such as acetone, methyl ethyl ketone, methyl isobutyl ketone or cyclohexanone; amides such as N,N-dimethylformamide, N,N-dimethylacetamide, N-methylformanilide, N-methylpyrrolidone or hexamethylphosphoramide; sulphoxides such as dimethyl sulphoxide, or sulphones such as sulpholane. Particular preference is given to using methyl tert-butyl ether, toluene, xylene, dichloroethane, dichloromethane, chlorobenzene, cyclohexane or methylcyclohexane, very particular preference to using toluene, xylene, THF, $CH_2Cl_2$, dichloroethane, methyl tert-butyl ether.

Steps 3 and 4

In a preferred embodiment of the process according to the invention, the 1-ayl-5-(trihalomethyl)-1H-pyrazole of the formula (V) is converted directly to the 3-(hydroxymethyl)-1-(pyridin-2-yl)-1H-pyrazole-5-carboxylic acid of the formula (VII).

The reaction time may, depending on the batch size and temperature, be selected within a range between one hour and several hours.

Steps 6 and 9

In a further embodiment of the process according to the invention, the $R^4$ group is first detached (step 6). Subsequently, the hydrolysis of the trihalomethyl group is undertaken (step 9).

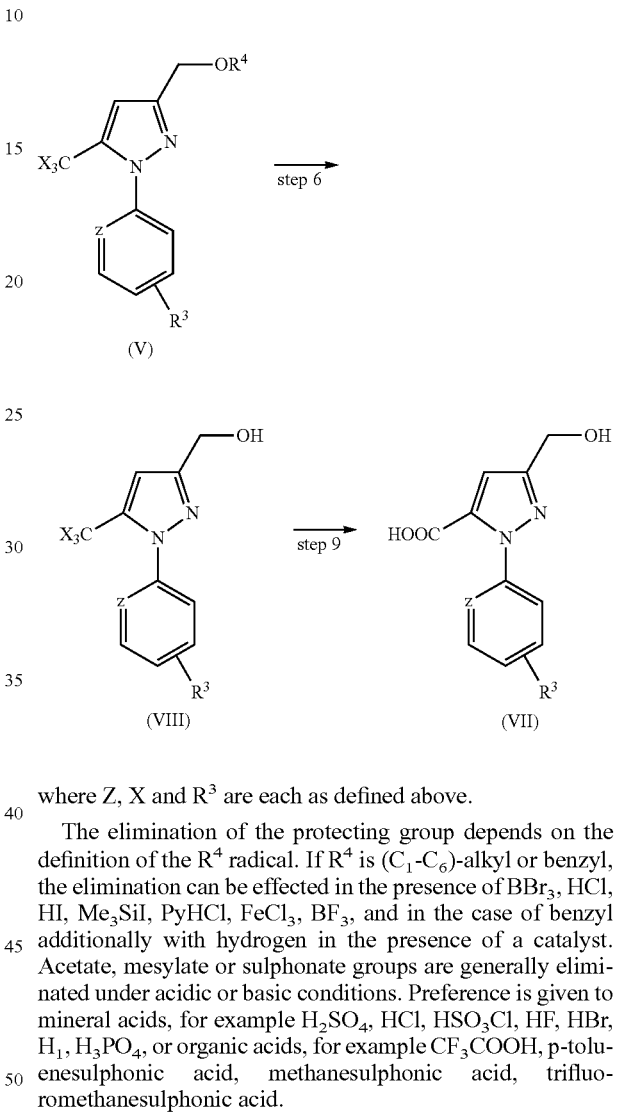

in which Z, X, $R^3$, $R^4$ are each as defined above.

The reaction is generally performed under acidic or basic conditions.

Preference is given to mineral acids, for example $H_2SO_4$, HCl, $HSO_3Cl$, HF, HBr, $H_1$, $H_3PO_4$, or organic acids, for example $CF_3COOH$, p-toluenesulphonic acid, methanesulphonic acid, trifluoromethanesulphonic acid.

The reaction can be accelerated by the addition of catalysts, for example $FeCl_3$, $AlCl_3$, $BF_3$, $SbCl_3$, $NaH_2PO_4$. The reaction can be performed in water only, without addition of acid.

Basic hydrolysis is effected in the presence of organic bases such as trialkylamines, alkylpyridines, phosphazines and 1,8-diazabicyclo[5.4.0]undecene (DBU), inorganic bases such as alkali metal hydroxides, for example lithium, sodium or potassium hydroxide, alkali metal carbonates ($Na_2CO_3$, $K_2CO_3$) and acetates such as NaOAc, KOAc, LiOAc, alkoxides, for example NaOMe, NaOEt, NaOt-Bu, KOt-Bu.

The halogenation step of the invention (A) is performed preferably within a temperature range from 20° C. to 120° C., more preferably at temperatures of 30° C. to 110° C.

The process step (2) of the invention is generally performed under standard pressure. Alternatively, it is, however, also possible to work under reduced pressure or under elevated pressure (e.g. reaction in an autoclave with aqueous HCl).

where Z, X and $R^3$ are each as defined above.

The elimination of the protecting group depends on the definition of the $R^4$ radical. If $R^4$ is ($C_1$-$C_6$)-alkyl or benzyl, the elimination can be effected in the presence of $BBr_3$, HCl, HI, $Me_3SiI$, PyHCl, $FeCl_3$, $BF_3$, and in the case of benzyl additionally with hydrogen in the presence of a catalyst. Acetate, mesylate or sulphonate groups are generally eliminated under acidic or basic conditions. Preference is given to mineral acids, for example $H_2SO_4$, HCl, $HSO_3Cl$, HF, HBr, $H_1$, $H_3PO_4$, or organic acids, for example $CF_3COOH$, p-toluenesulphonic acid, methanesulphonic acid, trifluoromethanesulphonic acid.

The elimination can also be performed without addition of acids or bases on heating in water.

Basic hydrolysis is effected generally with cheap inorganic bases such as alkali metal hydroxides, e.g. lithium, sodium or potassium hydroxide, alkali metal carbonates ($Na_2CO_3$, $K_2CO_3$), and acetates such as NaOAc, KOAc, LiOAc, alkoxides, for example NaOMe, NaOEt, NaOt-Bu, KOt-Bu. Organic bases such as trialkylamines, alkylpyridines, phosphazenes and 1,8-diazabicyclo[5.4.0]undecene (DBU) can also be used.

Step 8

If $R^4$ is alkyl or benzyl, the $CX_3$ group can be converted directly to the ester group. It is thus possible to convert compounds of the formula (V) directly to the compounds of the formula (I) (step 8),

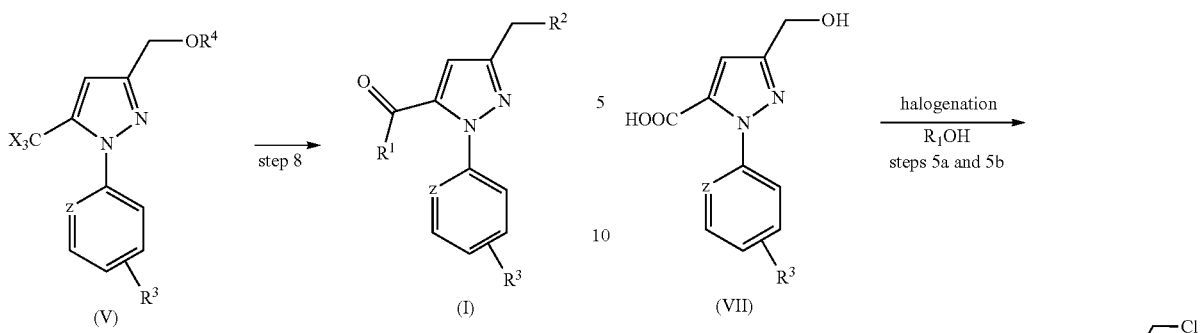

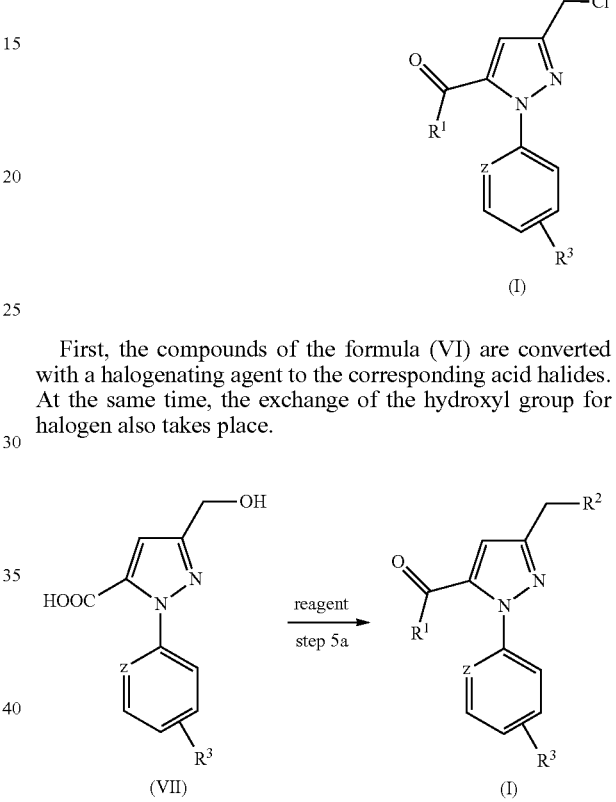

where
X, $R^3$, Z are each as defined above,
$R^1$ is $(C_1-C_6)$-alkoxy,
$R^1$ is preferably methoxy, ethoxy, propoxy,
$R^2$ is $(C_1-C_6)$-alkoxy, aryl$(C_1-C_6)$-alkoxy,
$R^2$ is preferably aryl$(C_1-C_6)$-alkoxy.

For these purposes, for example, alcohols are used, for example methanol, ethanol, propanol, or the alcohol/HCl, alcohol/FeCl$_3$, alcohol/H$_2$SO$_4$ or alcohol/alkoxide combinations.

Reaction step 8 can be performed in substance or in a solvent. Preference is given to performing the reaction in a solvent. Suitable solvents are, for example, selected from the group consisting of water, aliphatic and aromatic hydrocarbons, for example n-hexane, benzene or toluene, which may be substituted by fluorine and chlorine atoms, such as methylene chloride, dichloroethane, fluorobenzene, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides such as dimethylformamide (DMF) or N-methylpyrrolidone (NMP), or mixtures of such solvents, particularly suitable solvents being water, acetonitrile, dichloromethane.

If OR$^4$ is O(C=O)alk, OSO$_2$alk (compound of the formula (V)), the CX$_3$ group can be converted directly to the ester group. It is therefore possible to convert the compounds of the formula (V) directly to the compounds of the formula (I) $R^2$=OH (step 8).

Step 7

If OR$_4$ is OH (compound of the formula (VIII)), the CX$_3$ group can be converted directly to the ester group. It is thus possible to convert the compounds of the formula (VIII) directly to the compounds of the formula (I) $R^2$=OH (step 7). For these purposes, for example, alcohols are used, for example methanol, ethanol, propanol, or the alcohol/HCl, alcohol/FeCl$_3$, alcohol/H$_2$SO$_4$ or alcohol/alkoxide combinations.

Step 5

The compounds of the formula (VII) used in the performance of the process according to the invention are converted in a two-stage process to the compounds of the formula (I).

First, the compounds of the formula (VI) are converted with a halogenating agent to the corresponding acid halides. At the same time, the exchange of the hydroxyl group for halogen also takes place.

in which $R^1$ is halogen and $R^2$ is chlorine, bromine, fluorine.

To form the acid halides and to exchange hydroxyl for halogen, the following reagents are suitable: SOCl$_2$, POCl$_3$, oxalyl chloride, phosgene, diphosgene, POBr$_3$, PBr$_3$, SF$_4$, HCF$_2$CF$_2$N(Me)$_2$, PI$_3$. Preference is given to SOCl$_2$, oxalyl chloride, POCl$_3$, phosgene.

The halogenation step of the invention (step 5a) is performed preferably within a temperature range from −20° C. to +100° C., more preferably at temperatures of −10° C. to +70° C.

The process step of the invention is generally performed under standard pressure. Alternatively, it is, however, also possible to work under reduced pressure or under elevated pressure (e.g. reaction with phosgene).

The reaction time is not critical and may, depending on the batch size and temperature, be selected within a range between a few minutes and several hours.

In the performance of the process step of the invention, 1 mol of the acid of the formula (VII) is reacted with 1.9 mol to 2.5 mol, preferably 1.95 mol to 2.2 mol, more preferably with the equimolar amount (2 eq), of the chlorinating agent.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide. Particular preference is given to using toluene, xylene, chlorobenzene, n-hexane, cyclohexane or methylcyclohexane, methylene chloride, dichloroethane, very particular preference to using toluene, xylene, $CH_2Cl_2$, $ClCH_2CH_2Cl$.

In step 5b, the acid halides react with alcohol to form esters of the formula (I).

Preference is given to the alcohols such as methanol, ethanol, propanol, i-propanol, cyclohexanol.

The process step of the invention is preferably performed within a temperature range from −20° C. to +100° C., more preferably at temperatures of −10° C. to +40° C.

The reaction time is not critical and may, depending on the batch size and temperature, be selected within a range between a few minutes and several hours.

In the performance of the process step of the invention, 1 mol of the acid halide of the formula (VII) is reacted with 1 to 3 eq, preferably 1 eq of the alcohol. The reaction can be performed in alcohol as solvents. The halogenation and reaction with alcohol are generally performed as a one-pot reaction.

The inventive compounds of the formula (I) are valuable intermediates in the synthesis of anthranilamides (WO 2007/112893, WO 2007/144100).

PREPARATION EXAMPLES

Example 1

5-Bromo-1,1,1-trichloro-4-methoxypent-3-en-2-one was prepared by the method of Gerus et al., Synthesis 2001, 3, 431-436. Yield 90%.

Example 2

5,5,5-Trichloro-2-methoxy-4-oxopent-2-en-1-yl acetate 29.6 g (0.1 mol) of 5-bromo-1,1,1-trichloro-4-methoxypent-3-en-2-one, 17 g of potassium acetate, 5 g of tetrabutylammonium bromide and 8 g of acetic acid were stirred at 40° C. in 300 ml of acetonitrile for 16 h. The mixture was concentrated under reduced pressure, and the water was added to the residue. The product was extracted with ethyl acetate, the organic phase was washed with water and the solvent was removed completely under reduced pressure.

This gave 25.4 g (85%) of the product as a light-brown solid with the LC purity of 97%, m.p. 53-55° C.

$^1$H NMR (DMSO $d_6$) δ: 2.05 (s, 3H), 3.85 (s, 3H), 5.2 (s, 2H), 6.1 (s, 1H) ppm. GC/MS m/Z 275.

Example 3

[1-(3-Chloropyridin-2-yl)-5-hydroxy-5-(trichloromethyl)-4,5-dihydro-1H-pyrazol-3-yl]methyl Acetate 27.5 g (0.1 mol) of 5,5,5-trichloro-2-methoxy-4-oxopent-2-en-1-yl acetate and 14.4 g (0.1 mol) of 3-chloro-2-hydrazinopyridine were initially charged in 200 ml of ethanol, and the mixture was stirred at 25° C. for 3 h. The precipitate was filtered off and washed with cyclohexane.

This gave 34 g of the product (90% yield) as a white solid with a melting point of 105-106° C.

$^1$H NMR (DMSO $d_6$) δ: 2.07 (s, 3H), 3.30 (dt, 1H), 3.78 (dt, 1H), 4.79 (dt, 1H), 4.84 (dt, 1H), 7.23 (dd, 1H), 7.95 (dd, 1H), 8.22 (dd, 1H), 9.46 (br.s, 1H) ppm.

Example 4

1-(3-Chloropyridin-2-yl)-5-(trichloromethyl)-1H-pyrazol-3-yl]methyl Acetate 38.7 g of [1-(3-chloropyridin-2-yl)-5-hydroxy-5-(trichloromethyl)-4,5-dihydro-1H-pyrazol-3-yl]methyl acetate were dissolved in 200 ml of methyl tert-butyl ether, and 12.6 g of oxalyl chloride were added dropwise within 2 h (vigorous evolution of gas).

The mixture was stirred at 25° C. for a further 5 h and concentrated completely under reduced pressure.

This gave 36 g of the product as a viscous oil, which crystallized through after approx. 10 h at room temperature. m.p. 40° C.

$^1$H NMR (DMSO $d_6$) δ: 2.0 (s, 3H), 5.1 (dd, 2H), 7.0 (s, 1H), 7.6 (dd, 1H), 8.1 (dd, 1H), 8.5 (dd, 1H) ppm.

Example 5

[1-(3-Chloropyridin-2-yl)-5-(trichloromethyl)-1H-pyrazol-3-yl]methanol 36.9 g of 1-(3-chloropyridin-2-yl)-5-(trichloromethyl)-1H-pyrazol-3-yl]methyl acetate were dissolved in 100 ml of ethanol, and 20 g of NaOH (as a 40% solution in water) were added. After 1 h, the mixture was diluted with 300 ml of water, and the product was filtered off, washed with water and dried.

This gave 30 g (95%) of the product as a white solid. m.p. 109-111° C.

$^1$H NMR (DMSO $d_6$) δ: 4.55 (2H); 6.95 (1H); 7.55 (dd, 1H); 8.05 (dd, 1H); 8.5 (dd, 1H) ppm.

Example 6

Hydrochloride of 1-(3-chloropyridin-2-yl)-3-(hydroxymethyl)-1H-pyrazole-5-carboxylic Acid 38.7 g (0.1 mol) of [1-(3-chloropyridin-2-yl)-5-(trichloromethyl)-1H-pyrazol-3-yl]methanol and 10 g of $H_2SO_4$ (as a 10% solution in water) were stirred at 80° C. for 3 h.

The mixture was cooled to 0° C., and the precipitate was filtered off and washed with acetonitrile and dried.

Yield 90%. m.p. 173-175° C.

$^1$H NMR (DMSO $d_6$) δ: 3.5 (b.s, 1H) 4.50, (2H); 5.2 (b.s), 6.95 (1H); 7.55 (dd, 1H); 8.05 (dd, 1H); 8.5 (dd, 1H); 13 (b.s) ppm.

Example 7

2-[5-Carboxy-3-(hydroxymethyl)-1H-pyrazol-1-yl]-3-chloropyridiniumhydrogen Chloride The procedure is as in Example 6, except using 1-(3-chloropyridin-2-yl)-5-(trichloromethyl)-1H-pyrazol-3-yl]methyl acetate.

Yield 95%. m.p. 173-175° C.

Example 8

3-[(Benzyloxy)methyl]-1-(3-chloropyridin-2-yl)-1H-pyrazole-5-carboxylic Acid 4.4 g of 2-{3-[(benzyloxy)methyl]-5-(trichloromethyl)-1H-pyrazol-1-yl}-3-chloropyridine and 30 ml of 20% $H_2SO_4$ were heated at 100° C. for 24 h.

The precipitate was filtered off and washed with water. The yield was 92%.

$^1$H NMR (CDCl$_3$) δ: 4.61 (2H, s); 4.63 (m, 2H), 6.97 (1H, s); 7.2-7.4 (5H, m); 7.42 (1H, m); 7.96 [(1H, d, 2 Hz.)]; 8.5 [(1H, d, 2 Hz)] ppm.

Example 9

1-(3-Chloropyridin-2-yl)-3-(hydroxymethyl)-1H-pyrazole-5-carboxylic Acid Hydrochloride 3.43 g of 3-[(benzyloxy)methyl]-1-(3-chloropyridin-2-yl)-1H-pyrazole-5-carboxylic acid and 20 ml of HCl (37.5%) were heated at 100° C. for 2 h and then the reaction mixture was completely concentrated under reduced pressure at 10 mbar. This gave 1-(3-chloropyridin-2-yl)-3-(hydroxymethyl)-1H-pyrazole-5-carboxylic acid as the hydrochloride salt. Neutralization with NaHCO$_3$ afforded the free acid as a white solid. The yield was 94%.

Example 10

Methyl 3-(chloromethyl)-1-(3-chloropyridin-2-yl)-1H-pyrazole-5-carboxylate 1-(3-Chloropyridin-2-yl)-3-(hydroxymethyl)-1H-pyrazole-5-carboxylic acid hydrochloride 29 g (0.1 mol) was initially charged in 100 ml of toluene. 24 g SOCl$_2$ was added in portions at 60° C. The mixture was heated at 70° C. for 3 h, in the course of which the precipitate went completely into the solution. Methanol (30 ml) was slowly added dropwise to the mixture and the solution was stirred at 30° C. for another hour. Subsequently, the solution was concentrated under reduced pressure. This afforded 95% of the product with a purity of 96%.

$^1$H NMR (CDCl$_3$) δ: 3.7 (3H, s); 4.7 (2H, s); 7.1 (1H, s); 7.5 (1H, m); 8.05 [(1H, m)]; 8.5 [(1H, m)] ppm

Example 11

Methyl 1-(2-methylphenyl)-3-(hydroxymethyl)-1H-pyrazole-5-carboxylate 30.5 g of [1-(2-methylphenyl)-5-(trichloromethyl)-1H-pyrazol-3-yl]methanol and 300 ml of methanol were heated in an autoclave at 90° C. for 3 h. Methanol was removed under reduced pressure, and the product was purified by means of chromatography. Yield 80%.

Analytical Characterization $^1$H NMR (CD$_3$CN) δ: 7.4-7.2 (4H, m); 6.95 (1H, s), 4.55 (2H, s); 3.75 (3H, s); 11.95 (3H, s) ppm.

Example 12

Methyl 1-(3-chloropyridin-2-yl)-3-(hydroxymethyl)-1H-pyrazole-5-carboxylate 32.6 g of [1-(3-chloropyridin-2-yl)-5-(trichloromethyl)-1H-pyrazol-3-yl]methanol and 300 ml of methanol were heated in an autoclave at 90° C. for 3 h. Methanol was removed under reduced pressure, and the precipitate was washed with water. Yield 25 g, 94%. m.p. 104° C.

Example 13

Methyl 3-(chloromethyl)-1-(3-chloropyridin-2-yl)-1H-pyrazole-5-carboxylate

Methyl 1-(3-chloropyridin-2-yl)-3-(hydroxymethyl)-1H-pyrazole-5-carboxylate (26.7 g, 0.1 mol) was dissolved in 150 ml of CH$_2$Cl$_2$, and the solution was cooled to 5° C. SOCl$_2$ (0.12 mol) in 30 ml of CH$_2$Cl$_2$ was slowly added dropwise at this temperature. The mixture was stirred at 40° C. for a further 4 h and concentrated under reduced pressure. The product can be used further without purification.

Analytical Characterization $^1$H NMR (CD$_3$CN) δ: 8.52 (1H, d); 8.06 (1H, d), 7.55 (1H, dd); 7.10 (1H, s); 4.75 (2H, s); 3.75 (3H, s) ppm.

The invention claimed is:

1. A compound of the general formula (IV),

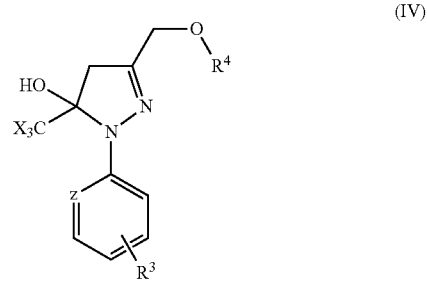

in which
X is fluorine, chlorine, bromine, or iodine;
R$^3$ is halogen, CN, NO$_2$, alkyl, cycloalkyl, haloalkyl, halocycloalkyl, alkoxy, haloalkoxy, alkylamino, dialkylamino, or cycloalkylamino;
Z is CH, or N; and
R$^4$ is (C═O)(C$_1$-C$_6$)-alkyl, or (C═O)halo(C$_1$-C$_6$)-alkyl.

2. A compound of the general formula (V), in which

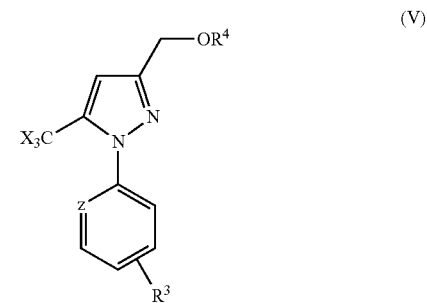

X is fluorine, chlorine, bromine, or iodine;
R$^3$ is halogen, CN, NO$_2$, alkyl, cycloalkyl, haloalkyl, halocycloalkyl, alkoxy, haloalkoxy, alkylamino, dialkylamino, or cycloalkylamino;

Z is CH, or N; and

R$^4$ is (C=O)(C$_1$-C$_6$)-alkyl, or (C=O)halo(C$_1$-C$_6$)-alkyl.

3. A compound of the general formula (IV) according to claim 1, wherein

R$^4$ is (C=O)CH$_3$ and X is chlorine.

4. A compound of the general formula (V) according to claim 2, wherein

R$^4$ is (C=O)CH$_3$ and X is chlorine.

* * * * *